(12) United States Patent
Robinson et al.

(10) Patent No.: US 11,007,084 B2
(45) Date of Patent: May 18, 2021

(54) MOISTURE ABSORBING SEAL

(71) Applicant: KCI Licensing, Inc., San Antonio, TX (US)

(72) Inventors: Timothy Mark Robinson, Shillingstone (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 135 days.

(21) Appl. No.: 15/788,013

(22) Filed: Oct. 19, 2017

(65) Prior Publication Data

US 2018/0036178 A1 Feb. 8, 2018

Related U.S. Application Data

(62) Division of application No. 14/104,630, filed on Dec. 12, 2013, now Pat. No. 9,833,363.

(Continued)

(51) Int. Cl.
*A61F 13/02* (2006.01)
*A61F 13/00* (2006.01)
*A61M 1/00* (2006.01)

(52) U.S. Cl.
CPC ...... *A61F 13/022* (2013.01); *A61F 13/00068* (2013.01); *A61F 13/0216* (2013.01);
(Continued)

(58) Field of Classification Search
CPC combination set(s) only.
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

"Injection molding of liquid silicone rubber"; Wikipedia, 2019, Wikipedia.org; https://en.wikipedia.org/wiki/Injection_molding_of_liquid_silicone_rubber (Year: 2019).*
(Continued)

*Primary Examiner* — Guy K Townsend (57) ABSTRACT

A sealing drape may be suitable for use with a reduced-pressure treatment system for treating a tissue site. The sealing drape may have an interior surface adapted for positioning adjacent to a peripheral surface of the tissue site. The sealing drape may include a sealing material and an absorbent material. The sealing material may be hydrophobic and substantially free of hydrophilic components. Further, the sealing material may be positioned between the interior surface of the sealing drape and the absorbent material. The sealing drape may be used with a manifold for positioning at the tissue site, a reduced-pressure interface, and a reduced-pressure source. Methods of manufacture and treatment are also disclosed.

27 Claims, 5 Drawing Sheets

Related U.S. Application Data (60) Provisional application No. 61/748,711, filed on Jan. 3, 2013.

(52) U.S. Cl.
CPC ....... *A61F 13/0223* (2013.01); *A61M 1/0088* (2013.01); *Y10T 156/10* (2015.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Guiles, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,356,405 A * | 10/1994 | Thompson ........ A61F 13/15203 604/358 |
| 5,358,494 A | 10/1994 | Svedman |
| 5,429,591 A * | 7/1995 | Yamamoto ............ A61F 13/023 424/448 |
| 5,437,622 A | 8/1995 | Carion |
| 5,437,651 A | 8/1995 | Todd et al. |
| 5,527,293 A * | 6/1996 | Zamierowski .......... A61F 5/453 128/898 |
| 5,549,584 A | 8/1996 | Gross |
| 5,556,375 A | 9/1996 | Ewall |
| 5,607,388 A | 3/1997 | Ewell |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,503,526 B1 * | 1/2003 | Krzysik ............... A61K 8/0208 424/402 |
| 6,553,998 B2 | 4/2003 | Heaton et al. |
| 6,746,765 B1 * | 6/2004 | Fattman ............... A61L 15/225 428/315.7 |
| 6,756,520 B1 * | 6/2004 | Krzysik ............... A61F 13/8405 604/359 |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,425,478 B2 * | 4/2013 | Olson ................... A61M 27/00 604/313 |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 9,833,363 B2 * | 12/2017 | Robinson ............ A61M 1/0088 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0241215 A1 * | 12/2004 | Lipman ............... A61F 13/0246 424/445 |
| 2005/0136773 A1 * | 6/2005 | Yahiaoui ............... D06M 15/09 442/394 |
| 2005/0137539 A1 * | 6/2005 | Biggie ................ A61M 1/0096 604/313 |
| 2007/0225663 A1 * | 9/2007 | Watt .................... A61F 13/0213 604/313 |
| 2008/0114276 A1 * | 5/2008 | Janusson ............... A61F 13/069 602/46 |

(56) References Cited

U.S. PATENT DOCUMENTS

| | | | |
|---|---|---|---|
| 2009/0227969 A1* | 9/2009 | Jaeb | A61F 13/00063 604/313 |
| 2009/0312728 A1* | 12/2009 | Randolph | A61F 13/00068 604/319 |
| 2010/0069863 A1* | 3/2010 | Olson | A61M 1/0088 604/368 |
| 2011/0301556 A1* | 12/2011 | Lichtenstein | A61M 1/0088 604/319 |
| 2012/0066855 A1* | 3/2012 | Schmidt | B08B 1/00 15/209.1 |
| 2012/0109083 A1* | 5/2012 | Coulthard | A61M 1/0066 604/319 |
| 2012/0277699 A1* | 11/2012 | Randolph | A61F 13/00038 604/319 |
| 2014/0163491 A1 | 6/2014 | Schuessler et al. | |
| 2014/0188060 A1* | 7/2014 | Robinson | A61M 1/0088 604/319 |
| 2015/0080788 A1 | 3/2015 | Blott et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2477314 A | 8/2011 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2004103415 A2 | 12/2004 |
| WO | 2005056069 A1 | 6/2005 |
| WO | 2009124100 A1 | 10/2009 |
| WO | 2011130570 A1 | 10/2011 |
| WO | 2012156655 A1 | 11/2012 |
| WO | 2013033131 A1 | 3/2013 |

OTHER PUBLICATIONS

Japanese Notice of Rejection for corresponding Application No. 2015551686, dated Jun. 19, 2018.
Chinese Third Office Action for corresponding Application No. 2013800715506, dated May 8, 2019.
Extended European Search Report for Corresponding Application No. 192052942, dated Jan. 29, 2020.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and:Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic (56) References Cited

OTHER PUBLICATIONS

Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

\* cited by examiner

MOISTURE ABSORBING SEAL

RELATED APPLICATION

This application claims the benefit, under 35 USC § 119(e), of the filing of U.S. patent application Ser. No. 14/104,630, entitled "Moisture Absorbing Seal", filed Dec. 12, 2013, which claims priority to Provisional Patent Application Ser. No. 61/748,711, entitled "Moisture Absorbing Seal," filed Jan. 3, 2013, both of which are incorporated herein by reference for all purposes.

TECHNICAL FIELD

The following subject matter relates generally to tissue treatment systems and, more particularly, but not by way of limitation, to medical sealing drapes and systems including medical sealing drapes.

BACKGROUND

Known tissue treatment systems may use a sealing drape to provide a fluid seal about a tissue site requiring treatment. Sealing around particular anatomical areas of the tissue site can be complicated and a leak-free seal is often difficult to achieve and maintain. Typical sealing drape materials may lack a sufficiently conformable adhesive capable of flowing into creases and cracks around the tissue site to achieve a good seal. Current materials may also suffer from being unable to transfer moisture away from the tissue site. Thus, if the sealing drape remains in place for an extended period of time, moisture present near the tissue site can cause maceration of the tissue and the formation of leaks between the tissue site and the sealing drape. Accordingly, improvements to sealing and moisture transfer capabilities for sealing drapes are desirable.

SUMMARY

Shortcomings with certain aspects of known tissue treatment systems and methods utilizing sealing drapes are addressed as shown and described in a variety of illustrative, non-limiting embodiments herein. Other features and advantages of the illustrative embodiments will become apparent with reference to the drawings and detailed description that follow.

In some embodiments, a reduced-pressure system for treating a tissue site may include a manifold, a sealing drape, and a reduced-pressure interface. The manifold may be adapted to be positioned adjacent the tissue site and to distribute reduced pressure to the tissue site. The sealing drape may have an interior surface and an external surface. The interior surface of the sealing drape may be adapted to cover the manifold and the tissue site to provide a sealed space between the interior surface of the sealing drape and the tissue site. Additionally, the sealing drape may include a sealing material and an absorbent material. The sealing material may be hydrophobic and substantially free of hydrophilic components. The absorbent material may be associated with the sealing material such that the sealing material may be positioned between the interior surface of the sealing drape and the absorbent material. The reduced-pressure interface may be adapted to deliver reduced-pressure. The reduced-pressure interface may be in fluid communication with the sealed space and the manifold.

In some embodiments, a sealing drape for treating a tissue site may include an interior surface, an external surface, a sealing material, and an absorbent material. The interior surface may be adapted to be positioned adjacent a peripheral surface surrounding the tissue site and to overlap the peripheral surface to provide a sealed space between the sealing drape and the tissue site. The sealing material may include a fluid permeable, hydrophobic material substantially free of hydrophilic components. The absorbent material may be disposed in the sealing material such that the sealing material may be positioned between the interior surface of the sealing drape and the absorbent material. The absorbent material may be adapted to absorb fluid communicated through the sealing material.

In some embodiments, a method of manufacturing a sealing drape for treating a tissue site may include the steps of: providing a sealing material; providing an absorbent material; and disposing the absorbent material in the sealing material. The sealing material may be hydrophobic and substantially free of hydrophilic components.

In some embodiments, a reduced-pressure system for treating a tissue site may include a manifold, a sealing drape, and a reduced-pressure interface. The manifold may be adapted to be positioned adjacent the tissue site and to distribute reduced pressure to the tissue site. The sealing drape may have an interior surface and an external surface. The interior surface of the sealing drape may be adapted to be positioned adjacent a peripheral surface surrounding the tissue site and to cover the manifold and the tissue site to provide a sealed space between the interior surface and the tissue site. Further, the sealing drape may be adapted to extend beyond the tissue site and to overlap the peripheral surface. Additionally, the sealing drape may include a sealing material and an absorbent material. The sealing material may be hydrophobic and substantially free of hydrophilic components. The absorbent material may be associated with the sealing material such that the sealing material may be positioned between the interior surface of the sealing drape and the absorbent material. The reduced-pressure interface may be adapted to deliver reduced-pressure. The reduced-pressure interface may be in fluid communication with the sealed space and the manifold.

In some embodiments, a method for treating a tissue site may include the steps of positioning a sealing drape adjacent a peripheral surface surrounding the tissue site, the sealing drape extending beyond the tissue site and overlapping the peripheral surface; and transferring moisture away from the peripheral surface through the sealing drape.

BRIEF DESCRIPTION OF THE DRAWINGS

A more complete understanding of this specification may be obtained by reference to the following detailed description when taken in conjunction with the accompanying drawings wherein.

DETAILED DESCRIPTION OF ILLUSTRATIVE EMBODIMENTS

In the following detailed description of the illustrative, non-limiting embodiments, reference is made to the accompanying drawings that form a part hereof. Other embodiments may be utilized, and logical, structural, mechanical, electrical, and chemical changes may be made without departing from the scope of this specification. To avoid detail not necessary to enable those skilled in the art to practice the embodiments described herein, the detailed description may omit certain information known to those skilled in the art. The following detailed description is provided without limitation, and with the scope of the illustrative embodiments being defined by the appended claims.

Figure 1:
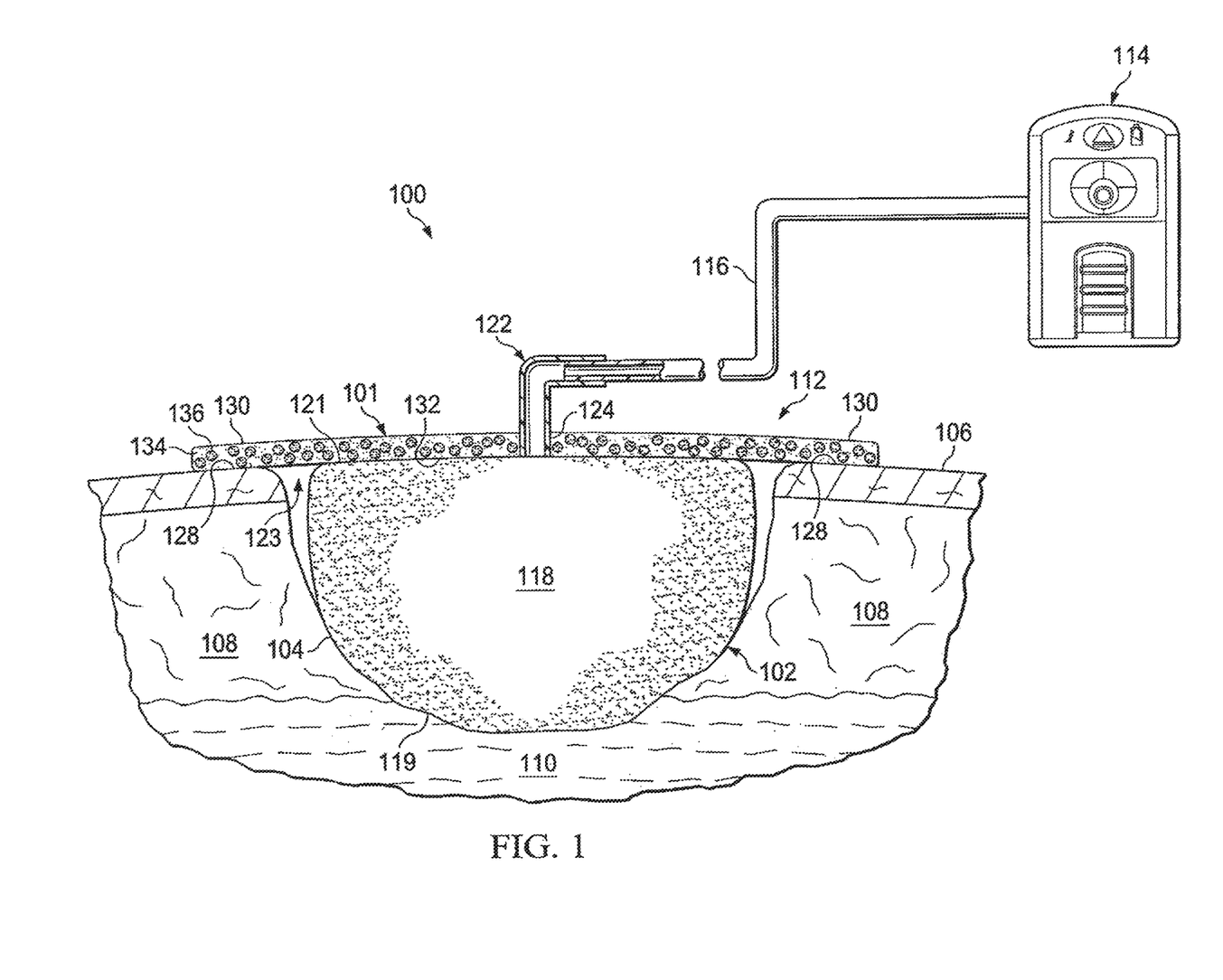
FIG. 1 is a side view, with a portion shown in cross section, of an illustrative embodiment of a reduced-pressure treatment system depicting an illustrative embodiment of a sealing drape.

Referring generally to the drawings, this specification provides a reduced-pressure treatment system 100 utilizing a sealing drape 101 for treating a tissue site 102. The reduced-pressure treatment system 100 is presented in the context of a tissue site 102 that may include, without limitation, a wound 104 extending through the epidermis 106, the dermis 108, and reaching into a hypodermis, or subcutaneous tissue 110. The reduced-pressure treatment system 100 may include a reduced-pressure dressing 112, a reduced-pressure source 114, and a reduced-pressure delivery conduit 116. The reduced-pressure delivery conduit 116 may provide reduced pressure from the reduced-pressure source 114 to the reduced-pressure dressing 112. As will be described below, the sealing drape 101 may be a component of the reduced-pressure dressing 112 that will provide a fluid seal with the tissue site 102 while preventing the surface of the tissue site 102 from becoming saturated with moisture.

The term "tissue site" in this context, for example, may refer to a wound or defect located on or within any tissue, including but not limited to, bone tissue, adipose tissue, muscle tissue, neural tissue, dermal tissue, vascular tissue, connective tissue, cartilage, tendons, or ligaments. A wound may include, without limitation, any irregularity with a tissue, such as an open wound, surgical incision, or diseased tissue. For example, the wound may include chronic, acute, traumatic, subacute, and dehisced wounds, partial-thickness burns, ulcers (such as diabetic, pressure, or venous insufficiency ulcers), flaps, and grafts. The term "tissue site" may also refer to areas of any tissue that are not necessarily wounded or defective, but are instead areas in which it is desired to add or promote the growth of additional tissue. For example, reduced pressure may be used in certain tissue areas to grow additional tissue that may be harvested and transplanted to another location.

In general, components of the reduced-pressure treatment system 100 may be coupled directly or indirectly. For example, the reduced-pressure source 114 may be directly coupled to the reduced-pressure dressing 112 or indirectly coupled to the reduced-pressure dressing 112 through the reduced-pressure delivery conduit 116. Components may be fluidly coupled to each other to provide a path for transferring fluids, such as liquid or gas, between the components. In some embodiments, components may be fluidly coupled with a tube. A "tube," as used herein, may refer to any tube, pipe, hose, conduit, or other structure with one or more lumina adapted to convey fluids between two ends. In some embodiments, components may be coupled by virtue of physical proximity, being integral to a single structure, or being formed from the same piece of material. Coupling may also include mechanical, thermal, electrical, or chemical coupling, such as a chemical bond.

"Reduced pressure" may refer to a pressure less than the ambient pressure at a tissue site being subjected to treatment. The reduced pressure may be less than the atmospheric pressure. The reduced pressure may also be less than a hydrostatic pressure at a tissue site. Unless otherwise indicated, values of pressure stated herein are gauge pressures. Consistent with the use herein, an increase in reduced pressure or vacuum pressure may refer to a relative reduction in absolute pressure.

The reduced-pressure source 114 may provide reduced pressure as a part of the reduced-pressure treatment system 100. The reduced-pressure source 114 may be any device for supplying a reduced pressure, such as a vacuum pump, wall suction, micro-pump, or other source. While the amount and nature of reduced pressure applied to a tissue site may vary according to the treatment application, the reduced pressure may be between about −5 mm Hg (−667 Pa) to about −500 mm Hg (−66.7 kPa). In some embodiments, the reduced pressure may be between about −75 mm Hg (−9.9 kPa) to about −300 mm Hg (−39.9 kPa).

As shown in FIG. 1, in some embodiments, the reduced-pressure dressing 112 may include a manifold 118, the sealing drape 101, and a reduced-pressure interface 122. The manifold 118 may have a first side 119 and a second side 121. The first side 119 of the manifold 118 may be placed within, over, proximate, adjacent, or in direct contact with the tissue site 102.

The manifold 118 maybe a substance or structure capable of applying reduced pressure to, delivering fluids to, or removing fluids from the tissue site 102. The manifold 118 may be positioned between the sealing drape 101 and the tissue site 102. The manifold 118 may be partially or fully in contact with the tissue site 102. The manifold 118 may partially or completely fill the tissue site 102, or the manifold 118 may be placed over the tissue site 102. The manifold 118 may take many forms, and may be any size, shape, or thickness depending on a variety of factors, such as the type of treatment being implemented or the nature and size of a particular tissue site. For example, the size and shape of the manifold 118 may be adapted to the contours of deep and irregular shaped tissue sites.

The manifold 118 may include a plurality of flow channels or pathways configured to distribute fluids to and remove fluids from the tissue site 102. In some embodiments, the flow channels or pathways may be interconnected to improve distribution of fluids provided to or removed from the tissue site 102. The manifold 118 may be a biocompatible material that is capable of being placed in contact with the tissue site 102 and distributing reduced pressure to the tissue site 102. For example, the manifold 118 may include, without limitation, devices that have structural elements arranged to form flow channels, such as cellular foam, open-cell foam, porous tissue collections, liquids, gels, and foams that include, or cure to include, flow channels. Additionally, the manifold 118 may be a gauze, felted mat, or any other material suited to a particular biological application.

In some embodiments, the manifold 118 may be a porous foam having interconnected cells or pores that act as flow channels. The porous foam may be, for example, a hydrophobic material, such as a polyurethane, open-cell reticulated foam manufactured under the trade name GranuFoam® by Kinetic Concepts, Inc. of San Antonio, Tex. In some embodiments, the manifold 118 may also be used to distribute fluids such as medications, antibacterials, growth factors, and various solutions to the tissue site 102. Other layers may be included in or on the manifold 118, such as absorptive materials, wicking materials, hydrophobic materials, and hydrophilic materials.

In some embodiments, the manifold 118 may be made from a hydrophilic material capable of wicking fluid away from the tissue site 102 while continuing to distribute reduced pressure to the tissue site 102. The wicking properties of the manifold 118 may draw fluid away from the tissue site 102 by capillary flow or other wicking mechanisms. An example of a hydrophilic foam may be a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics may include hydrophobic foams that have been treated or coated to provide hydrophilicity.

The manifold 118 may promote granulation at a tissue site when reduced-pressure is present within the reduced-pressure dressing 112. For example, any or all of the surfaces of the manifold 118 may have an uneven, coarse, or jagged profile that induce microstrains and stresses at the tissue site 102 when reduced pressure is applied through the manifold 118.

In some embodiments, the manifold 118 may be constructed from a bioresorbable material that may remain in a patient's body following use of the reduced-pressure dressing 112. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The manifold 118 may further serve as a scaffold for new cell-growth, or a scaffold material may be used in conjunction with the manifold 118 to promote cell-growth. A scaffold may be a substance or structure used to enhance or promote the growth of cells or formation of tissue, such as a three-dimensional porous structure that provides a template for cell growth. Illustrative examples of scaffold materials may include calcium phosphate, collagen, PLA/PGA, coral hydroxy apatites, carbonates, or processed allograft materials.

The sealing drape 101 may be adapted to cover the second side 121 of the manifold 118 and to seal to a peripheral surface 128 proximate the tissue site 102. Thus, the sealing drape 101 may provide a fluid seal between the reduced-pressure dressing 112 and the tissue site 102. "Fluid seal," or "seal," may refer to a seal adequate to maintain reduced pressure at a desired tissue site given the particular reduced-pressure source involved.

The peripheral surface 128 may be undamaged epidermis 106 peripheral to the tissue site 102. Thus, the sealing drape 101 may provide a sealed space 123 proximate to the tissue site 102 that is substantially isolated from the external environment, and capable of maintaining a reduced pressure provided by the reduced-pressure source 114. Reduced pressure applied through the manifold 118 in the sealed space 123 can promote healing by inducing macrostrain and microstrain in the tissue site 102, as well as by removing exudates and other fluids from the tissue site 102. Fluids from the tissue site 102 may be collected for disposal by a fluid canister (not shown) associated with the reduced-pressure source 114.

The sealing drape 101 may comprise an elastomeric material. "Elastomeric" may refer to the properties of an elastomer, such as a polymeric material that has rubber-like properties. More specifically, some elastomers have elongation rates greater than 100% and a significant amount of resilience. The resilience of a material may refer to the ability of the material to recover from an elastic deformation.

In some embodiments, the reduced-pressure dressing 112 may also include additional layers (not shown) positioned between the tissue site 102 and the sealing drape 101. For example, the reduced-pressure dressing 112 may further include an absorption layer, tissue-interface layer, or additional manifold layers. The reduced-pressure dressing 112 may also include an attachment device (not shown) capable of adhering or otherwise sealing the sealing drape 101 to the peripheral surface 128. Materials suitable for use as attachment devices for adhering the sealing drape 101 about a tissue site, may include, for example, silicones and hot-melt adhesives. Other attachment devices may include, for example, hydrogels and hydrocolloids.

Reduced pressure may be applied to the reduced-pressure dressing 112 through the reduced-pressure interface 122. The reduced-pressure interface 122 may be fluidly coupled to the sealing drape 101 through an aperture 124 in the sealing drape 101. In the illustrative example of FIG. 1, the aperture 124 is shown centrally located on the sealing drape 101. However, the aperture 124 may be located anywhere on the sealing drape 101, including without limitation, a peripheral portion of the sealing drape 101 that may be adjacent to an edge of the sealing drape 101. Although the aperture 124 is shown to be circular, the aperture 124 may have any shape. The shape of the aperture 124 may also be adapted to contour or substantially coordinate with the shape of the reduced-pressure delivery conduit 116. The reduced-pressure interface 122 may provide fluid communication between the sealed space 123 and the reduced-pressure delivery conduit 116 through the aperture 124.

The reduced pressure provided by the reduced-pressure source 114 may be delivered through the reduced-pressure delivery conduit 116 to the reduced-pressure interface 122. Thus, the reduced-pressure source 114 may be fluidly coupled to the reduced-pressure interface 122 by the reduced-pressure delivery conduit 116. In some embodiments, the reduced-pressure interface 122 may be a T.R.A.C.® Pad or Sensa T.R.A.C.® Pad available from Kinetic Concepts, Inc. of San Antonio, Tex. The reduced-pressure interface 122 may allow the reduced pressure to be delivered to the sealing drape 101 and realized within the sealed space 123 formed between the sealing drape 101 and the tissue site 102. In some embodiments, the reduced-pressure interface 122 may extend through the sealing drape 101 to the manifold 118, but numerous arrangements are possible. The reduced-pressure interface 122 may deliver the reduced pressure through the aperture 124 of the sealing drape 101 to the manifold 118 and the tissue site 102.

Upon application of the reduced pressure to the reduced-pressure dressing 112, fluids such as exudates from the tissue site 102 may be drawn into the manifold 118. Some amount of fluid as a consequence may also be brought into contact with the sealing drape 101, including portions of the sealing drape 101 that may be adjacent the peripheral surface 128 surrounding the tissue site 102. Moisture at the interface between the peripheral surface 128 and the sealing drape 101 may adversely affect the seal between the sealing drape 101 and the peripheral surface 128, and may increase the risk of maceration. "Maceration" or "macerating" may refer to the softening or breaking down of tissue as a result of prolonged exposure to moisture.

The sealing drape 101 of the reduced-pressure treatment system 100 can overcome these shortcomings and others by maintaining a fluid seal with the tissue site 102, while also preventing the peripheral surface 128 from becoming saturated with moisture. The sealing drape 101 may adhere to the tissue site 102 when wet or dry, may transmit and manage low levels of skin moisture to avoid maceration, and may be left in place for extended time periods.

Continuing with the embodiment of FIG. 1, the sealing drape 101 may have an external surface 130 and an interior surface 132. The interior surface 132 may be adapted to face the tissue site 102. As previously described, the sealing drape 101 may be adapted to sealingly engage the peripheral surface 128 to provide a sealed space 123 with the tissue site 102. The interior surface 132 of the sealing drape 101 may contact the peripheral surface 128 surrounding the tissue site 102 to provide the sealed space 123. The sealing drape 101 may also be stretchable or elastic in nature. The stretchable properties of the sealing drape 101 may facilitate placement of the sealing drape 101 proximate to tissue sites having a variety of shapes, topologies, or flexibility requirements. The sealing drape 101 may be sized to extend beyond the tissue site 102 to overlap the peripheral surface 128 surrounding the tissue site 102.

The sealing drape 101 may include a sealing material 134 and an absorbent material 136. The sealing material 134 may be fluid permeable, may provide a substantially sheet-like structure for the sealing drape 101, and may form a part of the interior surface 132 of the sealing drape 101. The absorbent material 136 may, for example, be contained within the sealing material 134, dispersed throughout the sealing material 134, or embedded as a sheet-like layer within the sealing material 134. The absorbent material 136 may be adapted to absorb moisture, such as exudate, from the tissue site 102 by drawing or wicking the fluid from the peripheral surface 128 of the tissue site 102.

The sealing material 134 may be comprised of any substantially pure hydrophobic material, and may have a variety of structures, including materials and structures that allow fluid, such as liquid or gas, to pass through the sealing material 134 without being absorbed by the sealing material 134. Herein, a substantially pure hydrophobic material may be substantially free of hydrophilic components due to the tendency for hydrophilic materials to retain fluid. For example, the substantially pure hydrophobic material of the sealing material 134 may not be a copolymer incorporating a hydrophilic component, such as a hydrophilic monomer. The sealing material 134, for example, may comprise a hydrophobic elastomer, such as a hydrophobic silicone elastomer. The hydrophobic characteristics of the sealing material 134 may prevent the sealing material 134 from directly absorbing fluid, such as exudate, from the tissue site 102, but may allow the fluid to pass through. Thus, the sealing material 134 may permit the passage of fluid away from the peripheral surface 128 and the tissue site 102 to substantially preclude any adverse affect on the seal being maintained with the tissue site 102. In this manner, the sealing material 134 may enhance the management of fluid in the reduced-pressure dressing 112 to allow for a continued fluid seal with the tissue site 102, while also protecting the tissue site 102 and surrounding areas from maceration.

The absorbent material 136 may be a hydrophilic material capable of absorbing fluid. The absorbent material 136 may be a separate and distinct component coupled with the sealing material 134 as described herein to provide the sealing drape 101. In some embodiments, the absorbent material 136 may comprise a super-absorbent material. For example, the absorbent material 136 may comprise one or more super-absorbent materials, such as, for example, carboxymethyl cellulose (CMC) or a carboxymethylcellulose salt, a cross-linked hydrophilic acrylic or a cross-linked hydrophilic acrylic salt, or an acrylamide.

When coupled with the sealing material 134, the absorbent material 136 may provide an absorption gradient to draw or otherwise wick fluid away from the tissue site 102. Fluid from the tissue site 102 may be drawn by the absorption gradient through the sealing material 134 and then be absorbed by the absorbent material 136. The absorbent material 136 may retain or bond to the fluid in conjunction with a physical or chemical change to the absorbent material 136. The absorbent material 136 may, for example, gel, increase in viscosity, or otherwise thicken upon contact with fluid from the tissue site 102, thereby trapping the fluid. The wicking properties of the absorbent material 136 may quickly draw fluid away from the tissue site 102, and thus, may prevent the accumulation of fluid at or near the tissue site 102. In a similar manner, the sealing material 134 may facilitate the evaporation of fluid absorbed by the absorbent material 136 or otherwise transferred through the sealing material 134 towards the external surface 130 of the sealing drape 101. Since fluid from the tissue site 102 may pass through the sealing material 134 to reach the absorbent material 136 as described above, the sealing material 134 may provide a separation between the tissue site 102 and the absorbent material 136. Thus, the sealing material 134 may be positioned between the interior surface 132 of the sealing drape 101 and the absorbent material 136. Further, the sealing material 134 may substantially preclude fluid that has been absorbed by the absorbent material 136 from contacting the tissue site 102 and the peripheral surface 128.

The sealing material 134 may have any size, shape, or thickness depending on a variety of factors, such as the type of treatment being implemented, the nature of the tissue site 102, or the peripheral surface 128. The thickness of the sealing material 134 may be increased or decreased to optimize the effectiveness of the sealing material 134 as a separator between the tissue site 102 and the absorbent material 136. For example, in applications in which the tissue site 102 is expected to release a large amount of fluid, a thicker sealing material 134 may be desirable to restrain or prevent the fluid from contacting the tissue site 102 or the peripheral surface 128. Conversely, a thinner sealing material 134 may be desirable in applications in which a lower amount of fluid is present. For example, the sealing material 134 may be between about 100 micrometers to about 200 micrometers in thickness. The thickness of the sealing material 134 may also be adjusted according to a desired ratio of the sealing material 134 to the absorbent material 136 comprising the sealing drape 101 depending on the application. In some embodiments, the overall thickness of the sealing drape 101 including the sealing material 134 and the absorbent material 136 may be about 250 micrometers.

Figure 2:
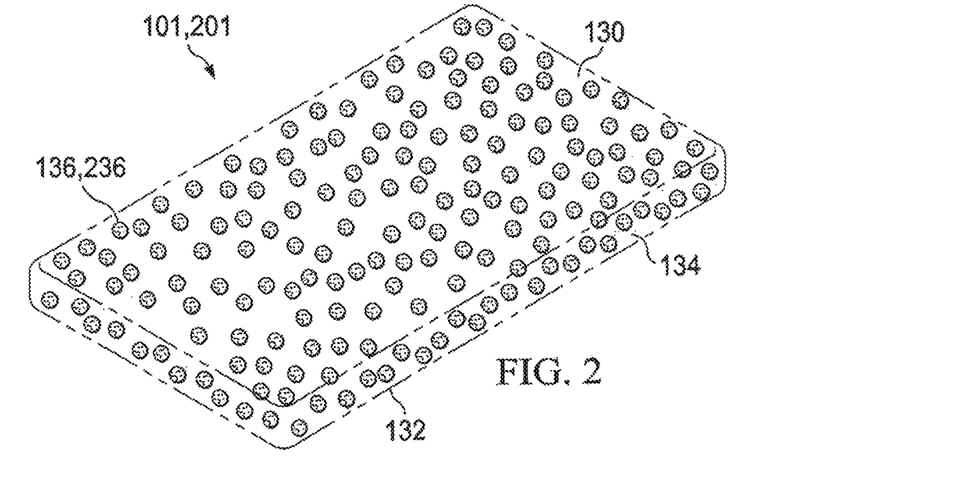
FIG. 2 is a perspective view of another illustrative embodiment of a sealing drape suitable for use with the reduced-pressure treatment system of FIG. 1.

The absorbent material 136 may be dispersed throughout and/or embedded as a sheet-like layer within the sealing material 134. FIG. 2 illustrates an embodiment of a sealing drape 201 that may include the sealing material 134 having absorbent particles 236 dispersed throughout the sealing drape 201. The absorbent particles 236 may provide the previously described absorbent material 136. The absorbent particles 236 may have any size or shape, depending on a variety of factors, such as the nature of the tissue site 102 or the amount of fluid anticipated to be released by the tissue site 102. In applications in which the tissue site 102 releases a large amount of fluid, larger absorbent particles 236 may be desirable to provide adequate absorptive capacity for the fluid.

Figure 3:
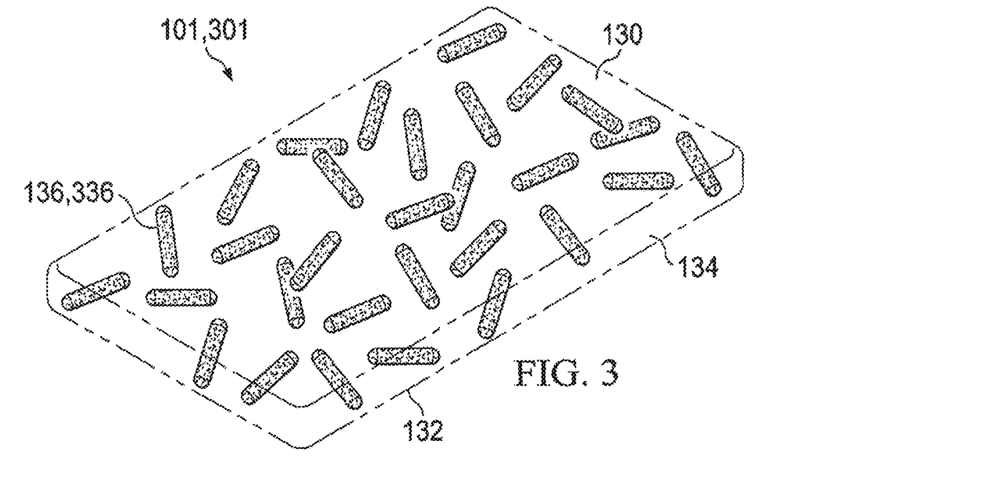
FIG. 3 is a perspective view of another illustrative embodiment of a sealing drape suitable for use with the reduced-pressure treatment system of FIG. 1.

FIG. 3 illustrates another embodiment of a sealing drape 301 in which absorbent fibers 336, such as elongate tubes, are dispersed throughout the sealing material 134. The absorbent fibers 336 may provide the previously described absorbent material 136. The absorbent fibers 336 may have any size or shape, depending on a variety of factors including the amount of fluid anticipated to be released by the tissue site 102. This specification contemplates embodiments including a mixture of absorbent particles 236 and absorbent fibers 336 dispersed within the sealing material 134 as described herein.

Figure 4:
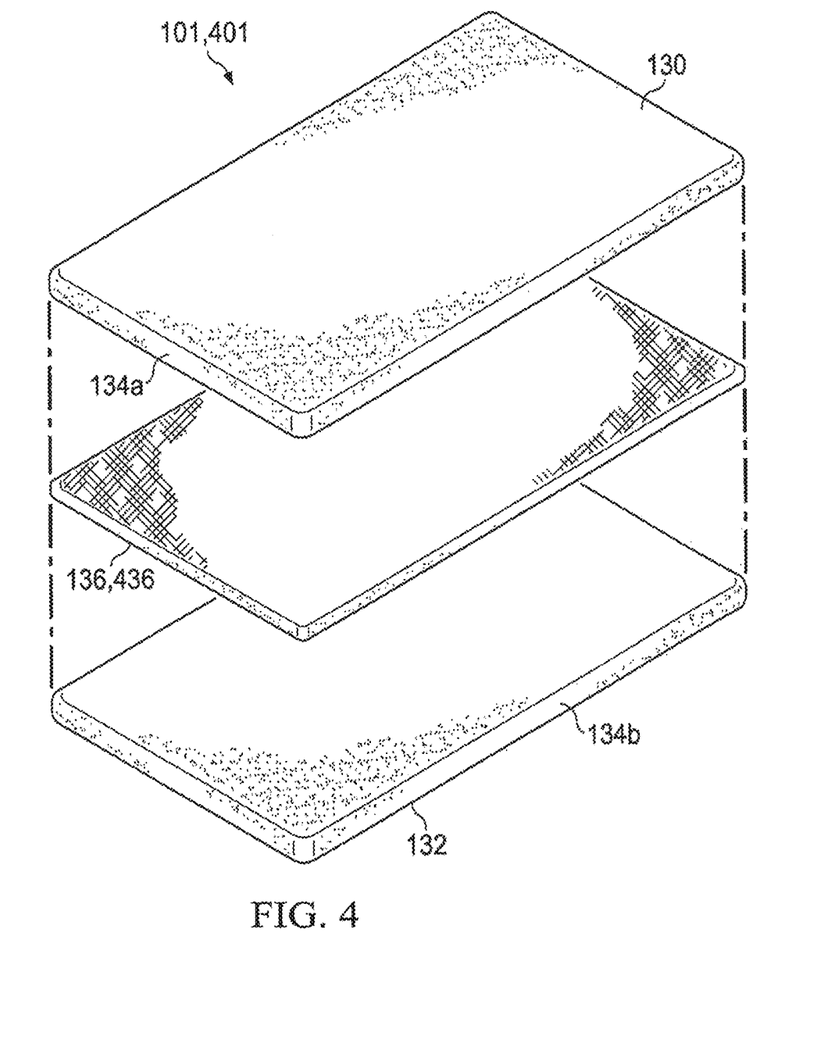
FIG. 4 is a perspective, exploded view of another illustrative embodiment of a sealing drape suitable for use with the reduced-pressure treatment system of FIG. 1.

FIG. 4 illustrates another embodiment of a sealing drape 401 in which the absorbent material 136 comprises an absorbent layer 436 positioned within the sealing material 134. The sealing drape 401 may include a first layer 134a of the sealing material 134 and a second layer 134b of the sealing material 134. The absorbent layer 436 may be positioned between the first layer 134a and the second layer 134b. The first layer 134a, the second layer 134b, and the absorbent layer 436 may each have the same or a different thickness. Thus, the absorbent layer 436 may be disposed at varying distances from the external surface 130 of the sealing drape 401 and the interior surface 132 of the sealing drape 401 depending on the thickness of each of the first and the second layer 134a, 134b.

The absorbent layer 436 may be provided as a nonwoven or a woven structure. For example, the absorbent layer 436 may comprise a nonwoven or a woven sheet of CMC fibers. Spaces or voids in the absorbent layer 436 may allow a reduced pressure that is applied to the reduced-pressure dressing 112 to be transferred within and through the absorbent layer 436.

Further, the absorbent layer 436 may have any size, shape, or thickness, depending on a variety of factors, such as the type of treatment being implemented or the nature of the tissue site 102. The size and shape of the absorbent layer 436 may be customized by a user to extend through a particular portion of the sealing drape 401. Thus, the absorbent layer 436 may be designed to cover a particular portion of the tissue site 102 or nearby tissue. For example, the width or thickness of the absorbent layer 436 may be increased to cause a corresponding increase in fluid storage capacity of the absorbent layer 436.

Referring to FIGS. 2-3, in some embodiments, the absorbent particles 236 and/or the absorbent fibers 336 may be dispersed or otherwise disposed throughout the sealing material 134 in a substantially uniform manner. A substantially uniform dispersion of the absorbent particles 236 and/or the absorbent fibers 336 may reduce the distance fluid must travel from the interior surface 132 before being absorbed. As described below, in some embodiments, utilizing a configuration for the sealing drape 101 that employs the absorbent particles 236 and/or the absorbent fibers 336 and/or the absorbent layer 436 may allow a user to customize the absorption gradient through the cross section of the sealing drape 101 for a desired application. Further, in some embodiments, the absorbent particles 236 and/or the absorbent fibers 336 may be dispersed or otherwise disposed within the sealing material 134 at a desired concentration and location within the sealing drape 101 to suit a particular application.

Figure 5:
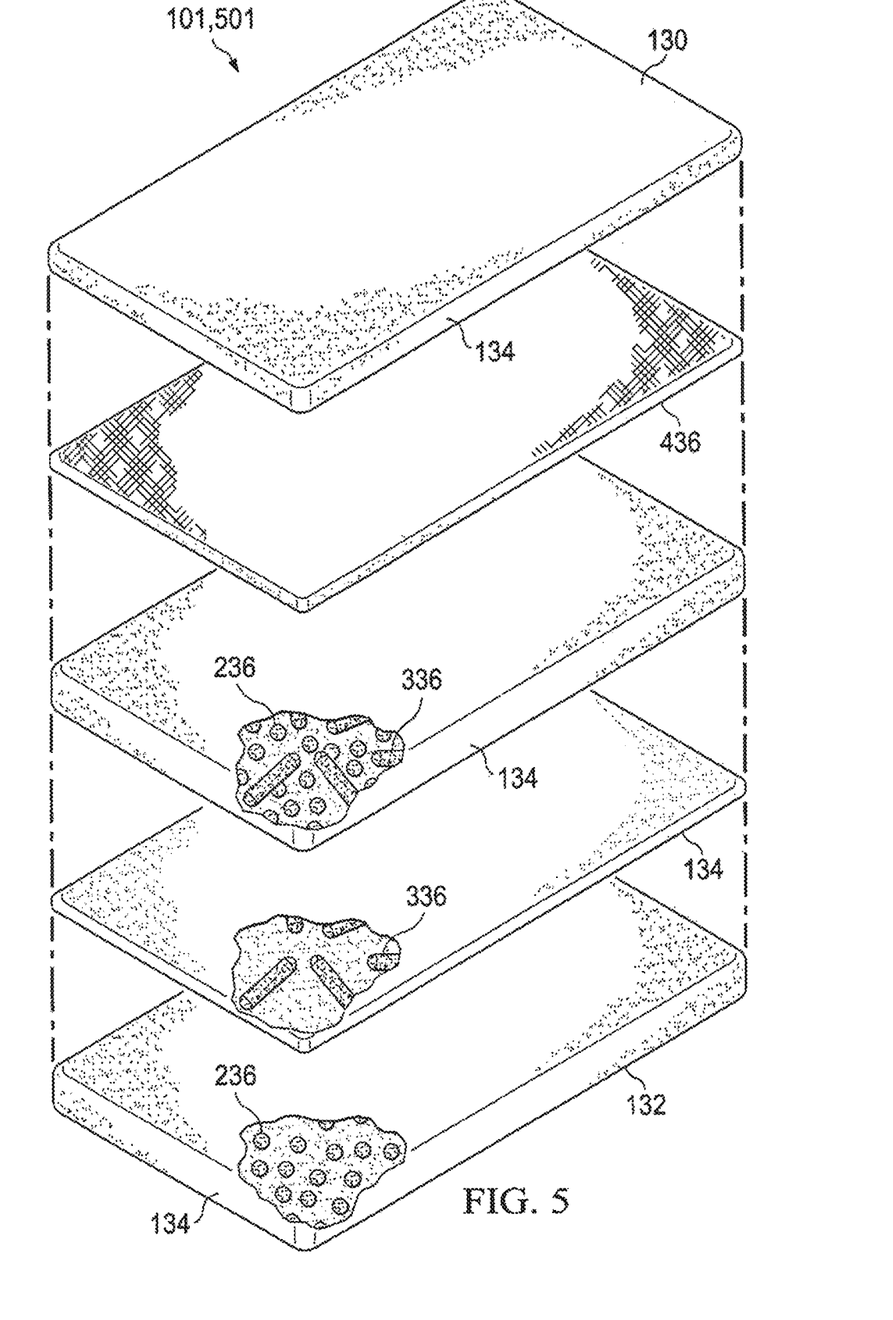
FIG. 5 is a perspective, exploded view of another illustrative embodiment of a sealing drape suitable for use with the reduced-pressure treatment system of FIG. 1.

FIG. 5 illustrates another embodiment of a sealing drape 501 that may have a plurality of the previously described absorbent materials 236, 336, 436 configured as described above with the sealing material 134. The absorbent materials 236, 336, 436 may be configured with the sealing member 134 as described, and positioned in layers relative to one another within the sealing drape 501. Further, the absorbent materials 236, 336, 436 may have the same or different dimensions and include the same or different absorbent properties. In some embodiments, the plurality of absorbent materials 236, 336, 436 may increase in concentration with increasing distance from the interior surface 132 of the sealing drape 501 through the cross section of the sealing drape 501, such as, for example, from the interior surface 132 toward the external surface 130. Similarly, the sealing drape 501 may have a higher ratio of the absorbent material 236, 336, 436 to the sealing material 134 with increasing distance from the interior surface 132. In some embodiments, the absorbent materials 236, 336, 436 may exhibit increasing hydrophilicity or absorbency with increasing distance from the interior surface 132. Further, in some embodiments, the plurality of absorbent materials 236, 336, 436 may be disposed within the sealing drape 501 such that the absorbent materials 236, 336, 436 positioned farthest from the interior surface 132 absorb more fluid than those closer to the interior surface 132. For example, the absorbent layer 436 positioned furthest away from the interior surface 132, as shown in FIG. 5, may have a higher fluid storage capacity than the absorbent materials 336, 236 positioned successively closer to the interior surface 132. In this manner, the plurality of absorbent materials 236, 336, 436 may provide a 3-dimensional network of absorbent material to enhance the transfer of moisture away from the tissue site 102 and to retain the moisture at a maximum distance away from the tissue site 102. This configuration may be customized as described to provide a desired absorptive gradient, Moisture Vapor Transmission Rate (MVTR), and fluid storage capacity to suit a particular application.

Figure 6:
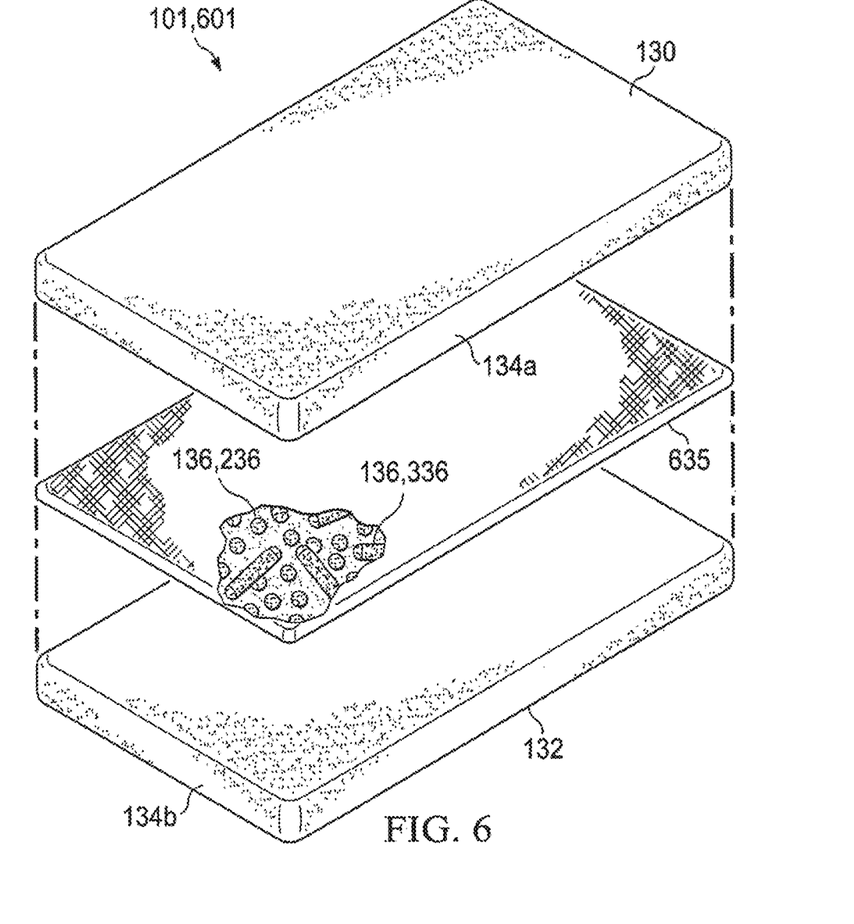
FIG. 6 is a perspective, exploded view of another illustrative embodiment of a sealing drape suitable for use with the reduced-pressure treatment system of FIG. 1.

FIG. 6 illustrates another embodiment of a sealing drape 601 that may include the absorbent material 136 carried by a carrier 635. The carrier 635 including the absorbent material 136 may be positioned within the sealing material 134. For example, similar to the sealing drape 401, the sealing drape 601 may include the first layer 134a and the second layer 134b of the sealing material 134. The carrier 635 may be positioned as a layer between the first layer 134a and the second layer 134b. Thus, the carrier 635 may provide a support structure that carries the absorbent material 136. The carrier 635 may comprise any of a variety of shapes and sizes, and may comprise any suitable nonwoven or woven material. In some embodiments, the carrier 635 may comprise a nonwoven hydrophobic polypropylene material that is formed into a sheet-like structure. The carrier 635 may provide support and strength for the absorbent material 136. In some embodiments, the absorbent material 136 may be dispersed within the carrier 635 as absorbent particles 236 and/or absorbent fibers 336.

The sealing drape 101, 201, 301, 401, 501, and 601 may be self-sealing to the tissue site 102, or may require an additional sealing device. As discussed above, in one embodiment, the sealing material 134 of the sealing drape 101, 201, 301, 401, 501, and 601 may comprise a hydrophobic silicone elastomer, which may function as a silicone adhesive and form a direct bond with the peripheral surface 128 of the tissue site 102, the epidermis 106, or the manifold 118.

In some embodiments, the reduced-pressure dressing 112 may include an additional attachment device (not shown) to fluidly seal the sealing drape 101, 201, 301, 401, 501, and

601 around the tissue site 102. The attachment device may be affixed to the interior surface 132 of the sealing drape 101, 201, 301, 401, 501, and 601 and may fluidly seal the sealing drape 101, 201, 301, 401, 501, and 601 to the epidermis 106 to provide the sealed space 123 surrounding the tissue site 102. The attachment device may cover at least a portion of the interior surface 132 of the sealing drape 101, 201, 301, 401, 501, and 601. Attachment devices may include, without limitation, a medically acceptable, pressure-sensitive adhesive that extends about a periphery, a portion of, or the entire sealing drape 101, 201, 301, 401, 501, and 601, a double-sided drape tape, paste, hydrocolloid, hydrogel, or similar sealing device. In this manner, the sealing drape 101, 201, 301, 401, 501, and 601 may be adapted to adhere to the peripheral surface 128 to secure the reduced-pressure dressing 112 to the tissue site 102.

In an illustrative embodiment of operation, the reduced-pressure treatment system 100 may be applied to a patient in the operating room after a surgical procedure or elsewhere. For example, the manifold 118 may be placed proximate to, within, overlying, or in contact with the tissue site 102. The sealing drape 101, 201, 301, 401, 501, and 601 may be placed over or otherwise covering the manifold 118 such that a portion of the sealing drape 101, 201, 301, 401, 501, and 601 overlays the peripheral surface 128 around the tissue site 102. The sealing drape 101, 201, 301, 401, 501, and 601 may be secured to the peripheral surface 128 in order to form a fluid seal between the tissue site 102 and the sealing drape 101, 201, 301, 401, 501, and 601. The fluid seal need only be adequate to allow the reduced-pressure treatment system 100 to maintain a reduced pressure on the tissue site 102 for a desired treatment time. The individual components of the reduced-pressure dressing 112 may be sized according to the particular application or the procedure being performed by a healthcare provider. For example, the components of the reduced-pressure dressing 112 may be sized, shaped, and configured to work in different anatomical applications such as the abdomen, chest, thighs, hip, and other locations.

The reduced-pressure interface 122 may be fluidly coupled to the sealing drape 101, 201, 301, 401, 501, and 601 before or after the installation of the sealing drape 101, 201, 301, 401, 501, and 601. The reduced-pressure conduit 116 may be fluidly coupled to the reduced-pressure interface 122. The reduced-pressure interface 122 may also be omitted and the reduced-pressure conduit 116 may be directly inserted into the sealing drape 101, 201, 301, 401, 501, and 601 in fluid communication with the sealed space 123. The reduced-pressure conduit 116 may be fluidly coupled to the reduced-pressure source 114. The reduced-pressure source 114 may be activated to deliver reduced pressure to the sealed space 123 provided by the sealing drape 101, 201, 301, 401, 501, and 601 surrounding the tissue site 102. In some embodiments, the reduced-pressure source 114 may be a micro-pump in or on the reduced-pressure dressing 112.

Upon application of the reduced pressure to the reduced-pressure dressing 112, exudates or other fluids from the tissue site 102 may be drawn into the manifold 118, the sealing drape 101, 201, 301, 401, 501, and 601, and through the reduced-pressure interface 122. As fluids are drawn from the tissue site 102, the peripheral surface 128 as well the components of the reduced-pressure dressing 112 may become moist, including the interior surface 132 of the sealing drape 101, 201, 301, 401, 501, and 601 where the sealing drape 101, 201, 301, 401, 501, and 601 contacts the peripheral surface 128 around the tissue site 102. Because of the ability of the sealing drape 101, 201, 301, 401, 501, and 601 to transfer moisture away from the peripheral surface 128 of the tissue site 102, the sealing drape 101, 201, 301, 401, 501, and 601 may maintain a fluid seal with the tissue site 102. The sealing drape 101, 201, 301, 401, 501, and 601 may allow fluid to pass through the interior surface 132 of the sealing drape 101, 201, 301, 401, 501, and 601 to reach the absorbent material 136 contained within the sealing material 134 of the sealing drape 101, 201, 301, 401, 501, and 601, thus helping to prevent saturation of the tissue site 102 and possible maceration.

This specification also provides methods of manufacturing the sealing drape 101, 201, 301, 401, 501, and 601 for use with the reduced-pressure treatment system 100. In some embodiments, the method may include the steps of providing the sealing material 134, and disposing the absorbent material 136 within the sealing material 134. The absorbent material 136 may be the previously described absorbent particles 236, the absorbent fibers 336, the absorbent layer 436, or any combination thereof.

In embodiments utilizing the absorbent particles 236 and the absorbent fibers 336, such as the sealing drape 201, 301, the method may include the step of mixing the absorbent particles 236 and/or the absorbent fibers 336 within the sealing material 134 prior to curing or otherwise solidifying the sealing material 134. The method may further include the steps of forming the mixture of the absorbent particles 236 and/or the absorbent fibers 336 into a desired shape, such as a sheet, and curing or otherwise solidifying the mixture. In some embodiments, the absorbent particles 236 and/or the absorbent fibers 336 may be mixed within the sealing material 134 to provide a substantially uniform dispersion of the absorbent particles 236 and/or the absorbent fibers 336 within the sealing material 134. In some embodiments, the absorbent particles 236 and/or the absorbent fibers 336 may be mixed within the sealing material 134 to provide a desired concentration of the absorbent particles 236 and/or the absorbent fibers 336 within the sealing material 134 at desired location therein.

In embodiments utilizing the absorbent layer 436, such as the sealing drape 401, the method may include the steps of providing the first layer 134a of the sealing material 134 and providing the second layer 134b of the sealing material 134. The method may additionally include the steps of providing the absorbent layer 436, positioning the absorbent layer 436 between the first and the second layer 134a, 134b, and enclosing the first and the second layer 134a, 134b about the absorbent layer 436. In other embodiments, multiple layers of the sealing material 134 and the absorbent layers 436 may be utilized to suit a particular application.

In embodiments utilizing the carrier 635, such as the sealing drape 601, the method may include the step of carrying the absorbent material 136, such as the absorbent particles 236 and/or the absorbent fibers 336, with the carrier 635. For example, the absorbent particles 236 and/or the absorbent fibers 336 may be applied to the carrier 635 for support and retention by the previously described nonwoven or woven structure of the carrier 635. The method may additionally include the steps of providing the first layer 134a of the sealing material 134, and providing the second layer 134b of the sealing material 134. Further, the method may include the steps of positioning the carrier 635, including the absorbent material 136, between the first and the second layer 134a, 134b, and enclosing the first and the second layer 134a, 134b about the carrier 635. In some embodiments, multiple layers of the sealing material 134 and the carrier 635, including the absorbent material 136, may be utilized to suit a particular application.

Although the treatment system 100 has been disclosed in the context of certain illustrative, non-limiting embodiments, various changes, substitutions, permutations, and alterations can be made without departing from the scope of this specification as defined by the appended claims. Any feature described in connection to any one embodiment may also be applicable to any other embodiment.

We claim:

1. A sealing drape for treating a tissue site, the sealing drape comprising:
   an interior surface and an external surface, the interior surface adapted to be positioned adjacent a peripheral surface surrounding the tissue site and to overlap the peripheral surface to provide a sealed space between the sealing drape and the tissue site;
   a sealing material comprising a hydrophobic polymer, wherein at least a portion of the sealing material forms the interior surface and is configured to provide the sealed space between the interior surface and the peripheral surface surrounding the tissue site; and
   an absorbent material dispersed within the sealing material and separated from the interior surface by the portion of the sealing material that forms the interior surface,
   wherein the absorbent material is adapted to absorb fluid communicated through the sealing material from an interface between the interior surface and the peripheral surface surrounding the tissue site, such that the sealed space is provided while preventing the peripheral surface surrounding the tissue site from becoming saturated with moisture, and
   wherein the sealing material is configured to allow fluid to pass into and through the sealing material to the absorbent material without being absorbed by the sealing material; and
   wherein the sealing material is adapted to provide evaporation of fluid retained in the absorbent material through the external surface of the sealing drape.

2. The sealing drape of claim 1, the absorbent material dispersed substantially uniformly within the sealing material.

3. The sealing drape of claim 1, the absorbent material comprising a plurality of absorbent particles.

4. The sealing drape of claim 1, the absorbent material comprising a plurality of absorbent fibers.

5. The sealing drape of claim 1, the absorbent material configured to provide an absorptive gradient through the sealing drape.

6. The sealing drape of claim 1, further comprising a plurality of absorbent materials disposed in the sealing material of the sealing drape, the absorbent materials having an absorptive capacity that increases with increasing distance through a cross section of the sealing drape from the interior surface of the sealing drape.

7. The sealing drape of claim 1, wherein the sealing material comprises an elastomeric material.

8. The sealing drape of claim 1, wherein the hydrophobic polymer is silicone.

9. A method of manufacturing a sealing drape for treating a tissue site, the method comprising:
   providing a sealing material being hydrophobic and substantially free of hydrophilic components;
   providing an absorbent material; and
   disposing the absorbent material in the sealing material, wherein at least a portion of the sealing material is positioned between the absorbent material and an interior surface of the sealing drape, the interior surface of the sealing drape adapted to be positioned adjacent a peripheral surface of the tissue site to prevent a peripheral surface surrounding the tissue site from becoming saturated with moisture, and
   wherein the sealing material is configured to allow fluid to pass into and through the sealing material to the absorbent material without being absorbed by the sealing material; and
   wherein the sealing material is adapted to provide evaporation of fluid retained in the absorbent material through an external surface of the sealing drape.

10. The method of claim 9, the step of disposing the absorbent material in the sealing material comprising:
    mixing the absorbent material and the sealing material together to provide a substantially uniform dispersion of the absorbent material within the sealing material; and
    curing the mixture.

11. The method of claim 10, further comprising the step of forming a sheet-shaped layer from the mixture.

12. The method of claim 10, the absorbent material comprising a plurality of absorbent fibers.

13. The method of claim 10, the absorbent material comprising a plurality of absorbent particles.

14. A method for treating a tissue site, comprising:
    positioning a sealing drape adjacent a peripheral surface surrounding the tissue site, the sealing drape comprising an exterior surface and an interior surface, the interior surface adapted to be positioned adjacent the peripheral surface, the sealing drape extending beyond the tissue site and overlapping the peripheral surface;
    applying a reduced pressure through the sealing drape to the tissue site;
    transferring moisture away from the peripheral surface through the interior surface of the sealing drape; and
    trapping moisture in an absorbent material dispersed in a sealing material comprising a hydrophobic polymer, the sealing material disposed between the absorbent material and the interior surface of the sealing drape to prevent the peripheral surface surrounding the tissue site from becoming saturated with moisture;
    wherein the sealing material is configured to allow fluid to pass into and through the sealing material to the absorbent material without being absorbed by the sealing material; and
    wherein the sealing material is adapted to provide evaporation of fluid retained in the absorbent material through an exterior surface of the sealing drape.

15. The method of claim 14, wherein the sealing material is adapted to maintain a reduced pressure.

16. The method of claim 14, wherein the absorbent material is dispersed substantially uniformly within the sealing material.

17. The method of claim 14, wherein the absorbent material comprises a plurality of absorbent particles.

18. The method of claim 14, wherein the absorbent material comprises a plurality of absorbent fibers.

19. The method of claim 14, wherein the absorbent material is configured to provide an absorptive gradient through the sealing drape.

20. The method of claim 14, further comprising a plurality of absorbent materials associated with the sealing material, the plurality of absorbent materials having an absorptive capacity that increases with increasing distance through a cross section of the sealing drape from the interior surface of the sealing drape.

21. The method of claim 14, wherein the sealing material comprises a hydrophobic silicone elastomer.

22. The sealing drape of claim 1, wherein the absorbent material is disposed within the hydrophobic polymer.

23. The sealing drape of claim 1, wherein the hydrophobic polymer is disposed between the absorbent material and the interior surface.

24. The sealing drape of claim 1, wherein the sealing material is adapted to maintain a reduced pressure at the tissue site.

25. The sealing drape of claim 1, wherein the sealing material is permeable to vapor and adapted to maintain a reduced pressure at the tissue site.

26. The sealing drape of claim 1, wherein the sealing material is permeable to vapor, elastomeric, and adapted to maintain a reduced pressure at the tissue site.

27. The sealing drape of claim 1, wherein:
   the sealing material consists of a hydrophobic silicone elastomer; and
   the absorbent material is selected from a group consisting of carboxymethyl cellulose, a salt of carboxymethyl cellulose, a cross-linked hydrophilic acrylic, a cross-linked hydrophilic acrylic salt, and an acrylamide.

* * * * *